US010874796B2

(12) United States Patent
Tsoukalis (10) Patent No.: US 10,874,796 B2
(45) Date of Patent: Dec. 29, 2020

(54) DEVICE AND SYSTEM FOR LOCATING AND OPERATING A MEDICAL DEVICE (71) Applicant: MICREL Medical Devices S.A., Gerakas (GR)

(72) Inventor: Achilleas Tsoukalis, Gerakas (GR)

(73) Assignee: Micrel Medical Devices, S.A., Gerakas (GR)

(*) Notice: Subject to any disclaimer, the term of this patent is extended or adjusted under 35 U.S.C. 154(b) by 495 days.

(21) Appl. No.: 14/559,304

(22) Filed: Dec. 3, 2014

(65) Prior Publication Data
US 2015/0151051 A1 Jun. 4, 2015

(30) Foreign Application Priority Data

Dec. 3, 2013 (GR) ............................ 20130100670

(51) Int. Cl.
*G16H 40/20* (2018.01)
*G16H 40/63* (2018.01)
(Continued)

(52) U.S. Cl.
CPC .......... *A61M 5/1723* (2013.01); *G16H 20/17* (2018.01); *G16H 40/20* (2018.01); *G16H 40/63* (2018.01); *H04W 64/00* (2013.01)

(58) Field of Classification Search
USPC ........................................................ 705/2, 3
See application file for complete search history.

(56) References Cited

U.S. PATENT DOCUMENTS 7,162,368 B2 * 1/2007 Levi .................. G01C 5/06
701/300
7,261,691 B1 * 8/2007 Asomani ............... A61B 5/1112
128/920
(Continued)

FOREIGN PATENT DOCUMENTS

EP 0735498 A1 * 10/1996 ......... G06F 19/3406
WO WO 2005062231 A2 * 7/2005 ......... G06F 19/3406
WO WO-2005062231 A2 * 7/2005 ............ G06Q 50/22

OTHER PUBLICATIONS

European Search Report and References Cited for Application EP 14196141, dated Jul. 7, 2015.*
(Continued)

*Primary Examiner* — Aryan E Weisenfeld
*Assistant Examiner* — Joshua B Blanchette
(74) *Attorney, Agent, or Firm* — Bookoff McAndrews, PLLC (57) ABSTRACT A device for locating and operating a medical device having different operational modes is provided. The device comprises a first database, wherein from a plurality of different operational modes for the medical device and from a plurality of different geographical positions of use for operation of the medical device, a predetermined operational mode is assigned to a geographical position of use. A positioning means is adapted to be provided at the medical device and to determine the geographical position of the medical device, and a control means is connected to the positioning means and the database and is adapted to determine, by mapping the determined geographical position of the medical device with the geographical positions of use stored in the first database, the predetermined operational mode which is assigned to the geographical position where the
(Continued)

medical device is located, and to set the medical device to said predetermined operational mode.

20 Claims, 1 Drawing Sheet (51) Int. Cl.
    *A61M 5/172*     (2006.01)
    *H04W 64/00*     (2009.01)
    *G16H 20/17*     (2018.01)

(56) References Cited

U.S. PATENT DOCUMENTS

| | | | |
|---|---|---|---|
| 7,305,245 B2 | 12/2007 | Alizadeh-shabdiz et al. | |
| 7,414,988 B2 | 8/2008 | Jones et al. | |
| 7,433,694 B2 | 10/2008 | Morgan et al. | |
| 7,502,498 B2* | 3/2009 | Wen | G16H 40/67 |
| | | | 382/128 |
| 8,566,325 B1 | 10/2013 | Brewington | |
| 2004/0008123 A1* | 1/2004 | Carrender | G06K 19/07749 |
| | | | 340/8.1 |
| 2005/0148887 A1* | 7/2005 | Reiter | G06F 19/3418 |
| | | | 600/508 |
| 2005/0207381 A1* | 9/2005 | Aljadeff | H04W 4/02 |
| | | | 370/338 |
| 2007/0032220 A1* | 2/2007 | Feher | H04M 11/04 |
| | | | 455/404.1 |
| 2007/0233521 A1* | 10/2007 | Wehba | A61M 5/142 |
| | | | 705/3 |
| 2008/0033402 A1* | 2/2008 | Blomquist | G06F 19/3468 |
| | | | 604/890.1 |
| 2011/0050428 A1* | 3/2011 | Istoc | G16H 50/20 |
| | | | 340/573.1 |
| 2013/0179544 A1 | 7/2013 | Sainnsbury | |
| 2013/0331121 A1* | 12/2013 | Bandyopadhyay | G01S 5/0205 |
| | | | 455/456.1 |

OTHER PUBLICATIONS

Gu et al. "A Survey of Indoor Positioning Systems for Wireless Personal Networks", IEEE Communications Surveys & Tutorials, vol. 11, No. 1, First Quarter 2009 (Year: 2009).*

Rida et al. "Indoor location position based on Bluetooth Signal Strength", 2015 2nd International Conference on Information Science and Control Engineering (Year: 2015).*

Moran, "Single Room Indoor Positioning System", Dublin Institute of Technology, May 27, 2014 (Year: 2014).*

* cited by examiner

DEVICE AND SYSTEM FOR LOCATING AND OPERATING A MEDICAL DEVICE

TECHNICAL FIELD

The present invention relates to a device and system for locating and operating a medical device having different operational modes, such as an infusion pump.

BACKGROUND

In hospitals, portable medical devices are stored at certain places, taken to be used in different parts of the hospital and then returned. It is critical for the medical and nursing staff to locate the medical devices in particular before and after their use. Therefore, it is desirable for the medical and nursing staff as well as, if needed, for the patients and other relevant people to know where a medical device is to be found in particular if after use it has not been returned to its known place.

In order to facilitate the location of medical devices, the use of the classical GPS system has been considered. However, the classical GPS system does not work properly in a densely constructed area like a hospital or any other building.

Known from the prior art are geolocation applications by means of triangulation of mobile telephone and/or WiFi or WLAN signals. U.S. Pat. No. 8,566,325 B1 deals with the locating of 3D building structures. US 2013 0179544 A1 teaches to enable games depending on a location. U.S. Pat. No. 7,261,691 A discloses a location method for medical use. U.S. Pat. No. 7,414,988 A1, U.S. Pat. No. 7,433,694 A1 and U.S. Pat. No. 7,305,245 A1 each deal with a location of WiFi enabled devices by mapping WiFi access points.

Further known is the Google Maps Geolocation API service which uses information sent by devices including mobile telephone and/or WiFi receivers and gives the longitude and latitude by exact measurement (which, however, includes a positioning error in form of a circle around the position) for each set including service towers and/or WiFi access points. The advantage of using such a service is that one does not need to create a map of its own, since a map already comes along with this service. This is very practical in a hospital since in a hospital there are one or two SSI names and tens or hundreds of access points which are each provided with a MAC (Media Access Control) address and distributed between the available SSI. An advantage of using the Google Maps technology is that you do not need to know the exact position of each access point; but if you do so, then you may have your own geolocation by triangulation.

It is an object of the present invention to facilitate the use of medical devices and to reduce medical and operational errors.

It is a further object of the present invention to provide a location based configuration in a patient data management system.

SUMMARY

In order to achieve the above and further objects, according to a first aspect of the present invention, there is provided a device for locating and operating a medical device having different operational modes, such as an infusion pump, comprising a first database, wherein from a plurality of possible different operational modes for the medical device and from a plurality of possible different geographical positions of use where the medical device is to be operated a predetermined operational mode is assigned to a specific geographical position of use, a positioning means which is adapted to be provided at the medical device and to determine the actual geographical position of the medical device, and a control means which is connected to the positioning means and the databases and is adapted to determine, by mapping the determined actual geographical position of the medical device with the geographical positions of use stored in the first database, the predetermined operational mode which is assigned to the actual geographical position where the medical device is actually located, and to set the medical device to said predetermined operational mode.

The present invention provides for not only knowing where the medical device is actually located, but also for operating the medical device in dependency of its actual position. Namely, the medical device to be used in conjunction with the present invention has different operational modes which comprise predetermined alarm settings and/or device access codes and/or user interface settings and/or different kinds of automatic configuration and/or usage of drugs. Due to the present invention, the medical device is caused to be operated and, thus, to behave differently depending on each specific position where the medical device is actually located. This is realized by that from a plurality of possible different operational modes of the medical device a predetermined operational mode is assigned to a certain position of use where the medical device is to be operated, which is carried out in the first data base, and that the medical device is set to the predetermined operational mode as assigned to the position of use in the first data base where the medical device is actually located which is carried out by the control means. The operation of the medical device can be adapted to the conditions, needs and/or operating rules which are required at the actual position of use where the medical device is actually located. For example, the medical device may be operated in a hospital in a different manner from the patient's home, since the operation may be more complex in the hospital due to the presence of the medical and nursing staff than at home where the medical device is operated by the patient only who has not the same skill as the medical and nursing staff in a hospital. In order to assure such a different adjustment of the operation of the medical device, according to the present invention the recognition of the position of the medical device is used to automatically set the medical device to a predetermined operational mode in dependence of the position where the medical device is determined to be actually located. As a result, neither the medical and nursing staff nor the patient has to be taken care of whether or not the medical device operates in a correct manner since this is taken over by the present invention.

Embodiments and modifications of the present invention are defined in the dependent claims. The device may further comprise a second data base, wherein from a plurality of different available locations such as operation theatres, intensive care units, wards and other places in a hospital, living, bed and other rooms in a patient's home as well as stores, a certain location is assigned to a certain geographical position, and a processing means which is connected to the positioning means and the data bases and is adapted to determine, by mapping the determined actual geographical position of the medical device with the geographical positions of the different available locations stored in the second database, the specific location where the medical device is actually located. So, a lot of different available locations are defined which include care areas like operation theatres, intensive care units, wards and other places in a hospital, living, bed and other rooms in a patient's home as well as stores, wherein in the second data base each of the defined locations is assigned to a certain geographical position where the assigned location is positioned. For identifying the position of the medical device, a positioning means is used which is to be provided at the medical device and determines the actual geographical position of the medical device. From the actual geographical position it is determined the actual care area where the medical device is actually located; this is done by a processing means which maps the determined actual geographical position of the medical device with geographical positions of the different available locations like e.g. care areas as stored in the second data base. Therefore, by doing so, even if the medical device is lost it can be found everywhere, and hence the medical device is available at any time.

According to a modification of this embodiment, there is provided a third database connected to the processing means, wherein from a plurality of data such as protocols and/or drug libraries certain data are assigned to a specific location where the medical device is to be operated, and input means which is adapted to be provided at the medical device and to input data into the medical device, wherein the processing means is further adapted to transfer from the third database to the input means the data as assigned to the actual location where the medical device is located. So, it is assured that in particular critical data as drug libraries are downloaded through the input means into the medical device in dependence of the position of its use.

A geolocation means may be used as the positioning means, wherein geolocation is also called realtime location service (RTLS).

The positioning means can be adapted to receive and process at least one of WiFi or WLAN signals and/or cellular network signals, like e.g. 2G, 3G or 4G signals, and to determine the actual geographical position by triangulation of said signals.

According to a modification of the aforementioned embodiment, there are sensing means for measuring the strength of the signals, for example, from each source, and adapted to use the result of the measurement of the signal strength for improving the accuracy of the determined actual geographical position of the medical device. So, this embodiment deals with the use of individual measurements of the strength of access points.

According to a further modification, the positioning means comprises sensing means for measuring the strength of the signals, a fourth data base is provided wherein from a plurality of results of measurements of the signal strengths a certain signal strength or a certain pattern of signal strengths is assigned to a particular place within a specific location, and the processing means is connected to the fourth data base and is further adapted to identify, by mapping the actual result of measurement of the signal strength with signal strengths stored in the fourth data base, the particular place within the actual location where the medical device is actually located. So, this embodiment not only deals with the use of individual measurements of the strength of access points in general in order to improve the accuracy of the determined actual geographical position of the medical device, but also to assign from a plurality of different results of measurement of the signal strength a certain signal strength or a certain pattern of signal strengths to a particular place within a specific location. Such a particular place can be e.g. a certain cabinet, shelf, table or bed in a certain room within a certain ward area. If such a particular place is to be located within a location, it might happen that a first attempt of the locating process might give an error showing a position some meters away from the target which defines a particular place within the location. This results from that at least sometimes the system used is subject to some meters of error. So, the use of individual measurements of the signal strength leads to somewhat like a knowledge about these errors along with a correction so as to make the results of the positioning means and the processing means and, hence, the locating of the medical device more precise. Accordingly, a combination of determining the actual geographical position by triangulation of signals and measuring the strength of said signals is used so as to define a correction on the basis of the knowledge stored in the fourth data base, resulting in re-locating of the medical device to the correct position at the particular place within the area of the location, e.g. a certain bed in a certain room within a certain ward area, where actually the medical device is indeed to be found.

Additionally or alternatively a positioning service provider may be used so that the positioning means is adapted to process data from the positioning service provider. Such a positioning service provider can be e.g. Google with its Google geolocation API which provides a method for defining the geographical position based on signals. Using such a service involves not needing to know the exact location of each access point or transmitter, but otherwise a geolocation of its own can be carried out by triangulation which requires knowledge of the geographical location of each access point or transmitter. Additionally, a map service provider like Google Maps may be used to visually represent the geographical position on a map. Using such a map service provider provides for not needing to create a map, like a hospital map, of its own since this comes along with a service of the map service provider.

The processing means may be adapted to mark the actual geographical position of the medical device on a map. With respect thereto, it is also conceivable to create a map of its own.

In order to facilitate the retrieval of the medical device, the processing means is further adapted to determine a route taken by the medical device by recording a plurality of geographical positions of the medical device over a certain time interval. This measure provides that the carrier of the medical device, i.e. medical or nursing staff or a patient, can be tracked accordingly before or after the start of the treatment. According to a modification the processing means is adapted to record the route on a map.

In order to better identify the floor in a multi-story building where the medical device is actually located, an altimeter may be used which is adapted to be provided at the medical device, wherein the processing means is further adapted to receive signals from the altimeter and in accordance with the signals from the altimeter to identify the floor.

For confirming the actual position where the medical device is located it is conceivable to additionally use a scanning means which is adapted to scan the medical device, wherein in particular the scanning means is adapted to scan a barcode or a RFID. In the absence of such a scanning means, a confirmation of the determined actual location or another selected neighboring location is provided at the medical device, wherein a data base is gaining knowledge on occurred location errors and their correction.

Moreover, the positioning means may be adapted to be activated even if the medical device is de-activated. So, the medical device can enter somewhat like a 'state of sleep' and only the position determination function by the positioning means works. In other words, the medical device can be switched off whereas the positioning means continues still working.

Further, several kinds of alarms can be provided so as to reduce patient's discomfort.

According to an embodiment, an alarm means can be used which is adapted to be provided at the medical device and to give an alarm, and a fifth data base is connected to the processing means, wherein from a plurality of different alarms a particular alarm is assigned to a specific location where the medical device is to be operated, and the control means is further adapted to cause the alarm means to give an alarm corresponding to the particular alarm as assigned to the actual position in the fifth data base. So, since in this embodiment the kind of alarm depends upon the position where the medical device is actually located, a retrieval of the medical device is facilitated.

According to a further embodiment, an alarm means is used which is adapted to be provided at the medical device and to give an alarm, and a remote control means which is adapted to be taken by the patient or the medical and/or nursing staff and to activate the alarm means, wherein at least one of the alarm means and the remote control means is adapted to measure the distance therebetween and the alarm means is additionally adapted to change the alarm in case of a change of the distance. Also this embodiment facilitates the retrieval of the medical device since due to the change of the alarm in case of a change of the distance the patient or the medical and/or nursing staff is guided to the medical device.

According to a still further embodiment, an alarm means is used which is connected to the positioning means and is adapted to be provided at the medical device and to give an alarm in case the positioning means determines a change of the actual geographical position of the medical device. So, due to this kind of alarm means attention is drawn to the medical device if it is taken away e.g. by somebody who is not responsible.

The same alarm function can be realized by alternatively using an alarm means which is adapted to be provided at the medical device and to give an alarm, wherein the control means is further adapted to cause the alarm means to give an alarm in case the processing means determines a change of the actual geographical position of the medical device.

At least one of the data bases and/or the processing means and/or the control means can be connected to a server or at least partly including a server which in particular is operated at a place remote from the medical device.

Further embodiments and modifications of the present invention are defined in the dependent claims.

BRIEF DESCRIPTION OF THE DRAWINGS

Embodiments of the present invention will now be described with reference to the drawings, in which.

DETAILED DESCRIPTION

Figure 1:
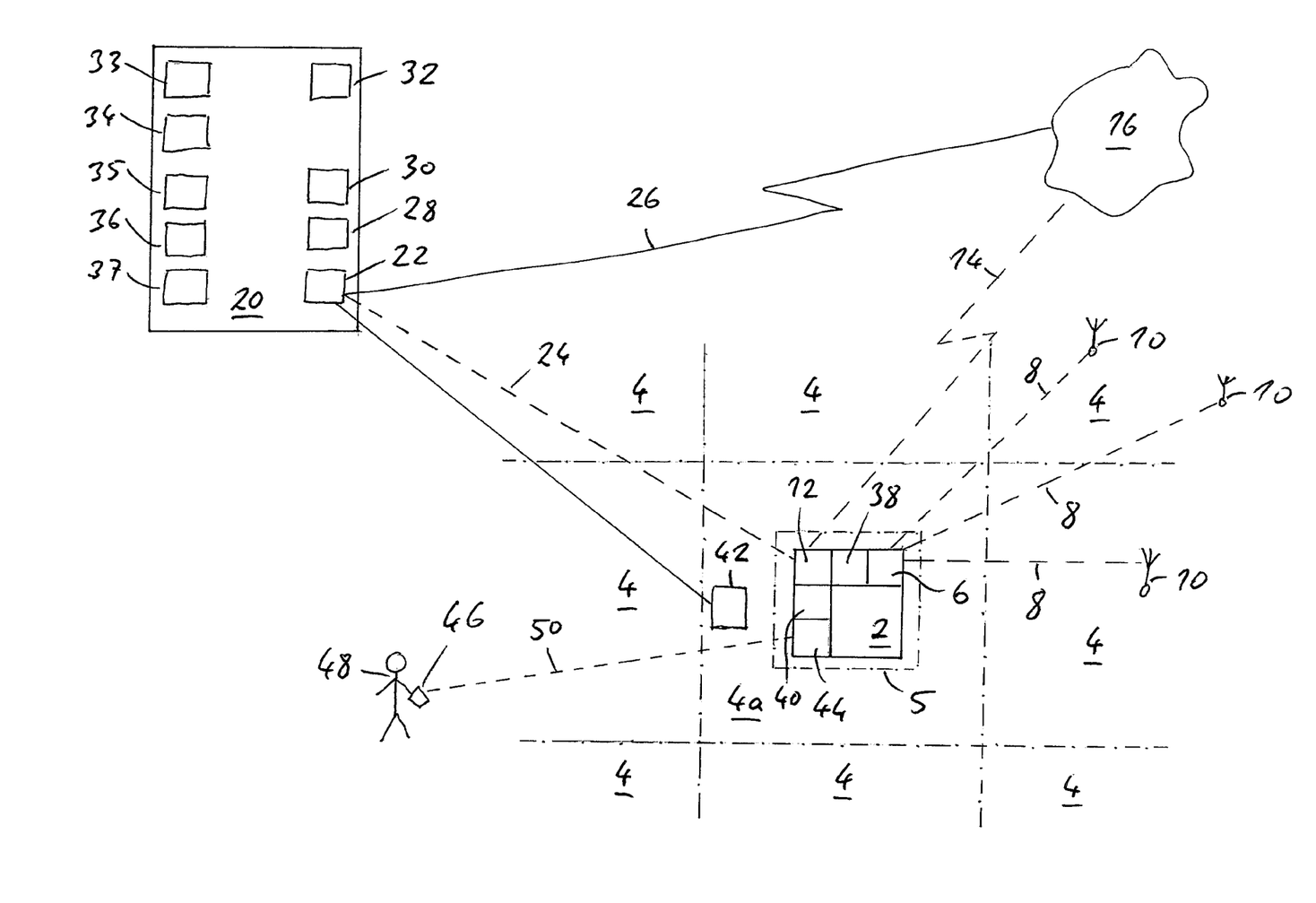
FIG. 1 is a schematic block diagram of a system for locating and operating a medical device according to embodiments of the present invention.

Schematically shown in FIG. 1 as a 'block' is a medical device 2 which is portable and used for medical purpose. The medical device 2 is optionally to be operated in different operational modes which comprise different kinds of automatic configuration and/or usage of drugs. For instance, the medical device 2 can be an infusion pump. The medical device 2 can be used optionally in a plurality of different locations which include care areas such as operation theatres, intensive care units, wards and other places in a hospital, living, bed and other rooms in a patient's home as well as stores. These locations are schematically characterized by dotted lines and designated by reference numeral "4" in FIG. 1, wherein the location where the medical device 2 is actually positioned is designated by the reference numeral "4a". As further schematically shown in FIG. 1, as an example the actual location 4a includes a particular place which is framed by a rectangle shown in dotted lines and designated by the reference numeral "5". This particular place 5 which concretely accommodates the medical device 2 can be e.g. a certain cabinet, shelf, table or bed in a certain room within a certain hospital ward area wherein said hospital ward area corresponds to the actual location 4a.

For identifying the position of the medical device 2, a positioning unit 6 is used which is attached at the medical device 2 and determines the actual geographical position of the medical device 2, wherein according to the schematic illustration of FIG. 1 the actual geographical position lies within the actual location 4a. The positioning unit 6 is provided to use a geolocation service which is also called realtime location service (RTLS), wherein the positioning unit 6 comprises receivers (not shown) for receiving telecommunication signals 8 from transmitters 10. The telecommunication signals 8 can be WiFi or WLAN signals and the transmitters 10 are access points and/or the telecommunication signals 8 are cellular network signals, which at the filing date have comprised 2G, 3G or 4G signals, and the transmitters 10 are the associated base tower stations. In order to determine the actual geographical position of the medical device 2 and, thus, the positioning unit 6, a triangulation of the telecommunication signals 8 is to be carried out. Therefore, the positioning unit 6 comprises a triangulation function. Further, in order to achieve an accurate triangulation result, it is required that the telecommunication signals 8 are to be transmitted from the transmitters 10 in different directions and the geographical position of each transmitter is known.

Moreover, the positioning unit 8 may be adapted to be activated even if the medical device 2 itself is de-activated. So, the medical device 2 can enter somewhat like a 'state of sleep' and only the position determination function by the positioning unit 6 is working. In other words, the medical device 2 can be switched off whereas the positioning unit 6 continues still working. This can be achieved by the provision of a separate battery which only supplies the positioning unit 6 with electrical power independently of the medical device 2. Alternatively, it is also conceivable to supply the positioning unit 6 with electrical power from the battery of the medical device 2 and to provide a switching circuit which interrupts the supply of electrical power from the common battery to at least the most power consuming elements or circuits of the medical device 2 or even to the whole medical device 2 and, thus, switches off said elements and circuits or the whole medical device 2 but at the same time continues supplying electrical power from the common battery to the positioning unit 6. With respect thereto, it is also conceivable to operate the positioning unit 6 in an intermittent mode wherein it is waked up every few minutes in order to measure the signals, and then sleeps again, since today's electronic circuitries usually consumes very little current with a few mA or even nA in a so-called sleep mode so that the battery capacity and autonomy is not really affected.

As further schematically shown in FIG. 1, provided at the medical device 2 is an interface 12 which is coupled with the medical device 2 and the positioning unit 6. The interface 12 is able to create a wireless data link 14 with the internet 16. Alternatively or additionally, if the telecommunication signals 8 are 3G or 4G signals, the mobile telecommunication system to which the telecommunication signals 8 are assigned can be used for building up a connection to the internet 16. Due to the connection to the internet 16, the service of a positioning service provider can be used wherein the positioning unit 6 is adapted to process data from the positioning service provider. Such a positioning service provider can be e.g. Google with its Google Maps geolocation. By using such a positioning service provider the creation of a map like a hospital map of its own is not needed since this comes along with the service of the positioning service provider.

For data processing outside of and separate from the medical device 2, the system comprises a server 20 as schematically shown in FIG. 1. Whereas the medical device 2 is portable and provided to be taken from one location 4 to another location 4 according to the need where the medical device 2 is to be operated, usually the server 20 is positioned stationary at a predetermined place. The server 20 includes an interface 22 which is connected to the interface 12 at the medical device 2 via a wireless data link 24. Further, the interface 22 of the server 20 is also adapted to build up a connection 26 with the Internet 16 so that the server 20 is also able to process data from a positioning service provider in a similar manner as described above.

As further schematically shown in FIG. 1, the server 20 comprises a processing unit 28, a control unit 30, an alarm unit 32, and first to fifth databases 33 to 37.

In the first data base 33 from a plurality of possible different operational modes, including predetermined alarm settings and/or device access codes and/or user interface settings and/or different kinds of automatic confirmation and/or usage of drugs, for the medical device 2 and from a plurality of possible different geographical positions of use or locations 4 where the medical device 2 is to be operated a predetermined operational mode is assigned to a specific geographical position of use or location 4. In the second data base 34 from a plurality of different available locations 4 such as operation theatres, intensive care units, wards and other places in a hospital, living, bed and other rooms in a patient's home as well as stores, a certain functional location 4 which comprises a care area is assigned to a certain geographical position. So, a lot of different available locations 4 are defined in the second data base 34 wherein each of the functional locations 4 is assigned to a certain geographical position which hence lies within the area of the assigned location 4.

The processing unit 28 which is inter alia connected to the interface 22 and the second data base 34 determines, by mapping the actual geographical position of the medical device 2 as determined by the positioning unit 6 with the geographical positions of the different available functional locations 4 stored in the second data base 34, the specific location 4a where the medical device 2 is actually located. So, from the actual geographically position it is determined the actual location 4a where the medical device 2 is actually located. Therefore, by doing so, even if the medical device 2 is lost it can be found everywhere, and hence the medical device 2 is available at any time.

However, the server 20 does not only know where the medical device 2 is actually located, but also controls the operation of the medical device 2 in dependency of it's actually location 4a. Namely, as already mentioned above, the medical device 2 is optionally to be operated in different operational modes which comprise different kinds of automatic configuration and/or usage of drugs. The server 20 causes the medical device 2 to be operated and, thus, to behave differently depending on each location 4. This is realized by that from a plurality of possible different operational modes of the medical device 2 a predetermined operational mode is assigned to a certain position of use or location 4 where the medical device 2 is to be operated, which is carried out in the first data base 33 as mentioned above, and that the medical device 2 is set to the predetermined operational mode as assigned to the actual position of use or location 4a in the first data base 33 where the medical device 2 is actually located which is carried out by the control unit 30. Namely, the operation of the medical device 2 is to be adapted to the conditions, needs and/or operational rules which are required in the actual location 4a where the medical device 2 is actually located. Usually, the medical device 2 may be operated in a hospital in a different manner from the patient's home, since the operation may be more complex in the hospital due to the presence of the medical and nursing staff than at home where the medical device 2 is operated by the patient only who has not the same skill as the medical and nursing staff in a hospital. In order to assure such a different adjustment of the operation of the medical device 2, the recognition of the position of the medical device 2 by means of the positioning unit 6 is used by the control unit 30 of the server 20 to automatically set the medical device 2 to a predetermined operational mode in dependence of the actual location 4a where the medical device 2 is actually located. The control unit 26 determines, by mapping the actual geographical position of the medical device 2 as determined by the positioning unit 6 with the geographical positions of use as stored in the first data base 29, the predetermined operational mode which is assigned to the actual geographical position or location 4a where the medical device 2 is actually located, and creates respective specific control signals for setting the medical device 2 to said predetermined operational mode. The specific control signals as generated by the control unit 26 in accordance with the desired predetermined operational mode are transferred from the interface 22 of the server 20 via the data link 24 to the interface 12 of the medical device 2 where the control data are input for setting the medical device 2 to the desired predetermined operational mode.

In the third data base 35 from a plurality of data such as protocols and/or drug libraries certain data are assigned to a specific location 4 where the medical device 2 is to be operated. The processing unit 28 causes the data as assigned to the actual location 4a where the medical device 2 is actually located to be transferred from the third data base 35 through the interface 22 of the server 20 and the data link 24 to the interface 12 at the medical device 2 where said data are downloaded into the medical device 2.

In order to improve the accuracy of the determined actual geographical position of the medical device 2 by the positioning unit 6, provided at the medical device 2 is a sensing unit 38 which measures the strength of the signals 8. The results of the measurement of the signal strength as determined by the sensing unit 38 are transferred through the interface 12 at the medical device 2, the data link 24 and the interface 22 of the server 20 to the processing unit 28 where they are further processed. With respect thereto, according to an embodiment as schematically shown in FIG. 1, in the fourth data base 36 from a plurality of results of measurement of the signal strengths as carried out by the sensing unit 38 a certain signal strength or a certain pattern of signal strengths is assigned to a particular place (e.g. "5") within a specific location (e.g. "4a"). By mapping the actual result of measurement of the signal strengths determined by the sensing unit 38 with signal strengths as stored in the fourth data base 36 the processing unit 28 identifies the particular place 5 within the actual location 4a where the medical device 2 is actually located. As already mentioned above, such a particular place 5 can be e.g. a certain cabinet, shelf, table or bed in a certain room within a certain ward area as defined by the actual location 4a. If such a particular place 5 lies within the actual location 4a, it might happen that a first attempt of the locating process might give an error showing a position some meters away from the target which defines the particular place 5 within the location 4a. This results from that at least sometimes the geolocation system is subject to some meters of error. So, the use of the individual measurements of the signal strength leads to somewhat like a knowledge about these errors as stored in the fourth data base 36 along with a correction carried out by the processing unit 28 in cooperation with the sensing unit 38 so as to make the results of the positioning unit 6 and, thus, the locating of the medical device 2 more precise. Further, in order to realize triangulation, the exact geographical position of each access point or transmitter 10 is stored in the fourth data base 36. Accordingly, a combination of determining the actual geographically position by triangulation of the signals 8 by means of the positioning unit 6 and measuring the strength of the signals 8 by means of the sensing unit 38 is used so as to define a correction on the basis of the knowledge stored in the fourth data base 36, resulting in somewhat like a re-locating of the medical device 2 to the correct position at the particular place 5 within the actual location 4a (e.g. a certain bed in a certain room within a certain ward area, where actually the medical device 2 is indeed to be found.

In order to better identify the floor in a multi-storey building which is defined by a location 4, but is not shown in detail in FIG. 1 where the medical device 2 is actually located, an altimeter 40 is additionally provided at the medical device 2. The data generated by the altimeter 40 are transferred to the interface 12 at the medical device 2, the data link 24 and the interface 22 of the server 20 to the processing unit 28 where these data are further processed so as to identify the floor in the building which partly or completely corresponds to the actual location 4a as shown in FIG. 1. The identification of the floor can also be carried out by access point mapping per geographical position (longitude and latitude) and altitude so that a three-dimensional triangulation is possible to locate a medical device 2 in a three-dimensional space.

The processing unit 28 is further adapted to mark the actual geographical position of the medical device 2 on a map. With respect thereto, it is also conceivable to create a map of its own. For storing such a map, the processing unit 28 includes a memory which is not shown in FIG. 1.

In order to facilitate the retrieval of the medical device 2, the processing unit 28 further determines a route taken by the medical device 2 by recording a plurality of geographical positions of the medical device 2 over a certain time interval wherein such a route may be recorded on a map.

For confirming the actual location 4a or the actual particular place 5 where the medical device 2 is located, additionally provided in the shown embodiment is a scanner 42 which is coupled to the interface 22 of the server 20. The scanner 42 is used to scan the medical device 2 and is in particular adapted to scan a barcode or a RFID. Also, the positioning unit 6 may ask the user whether the determined actual location (e.g. care area) 4a and particular place 5 (e.g. a particular bed) is correct and, if not, gives a choice of possible nearby locations 4 and particular places 5. So, the processing unit 28 in the server 20 learns, in particular by artificial intelligence, and corrects positioning errors next time by using the scanner 42 or user feedback on a screen and artificial intelligence. For doing so, it is advantageous to provide the processing unit 28 with neural networks (not shown). As an example, if an infusion is carried out two times in a specific bed in a certain ward on a particular floor, the system will correctly determine said bed for carrying out a third infusion even if there is some positioning error as previously. Such a correction process under increasing precision can be carried out even without knowledge of the exact position of the access points or transmitters 10 wherein a triangulation is done. This makes the system applicable directly in a hospital without any need of mapping the locations of the access points or transmitters 10 wherein the precision of a correct location determination is gradually increased. With the increase of the system accuracy, the aforementioned scanning and feedback becomes gradually needless.

In the embodiment as schematically shown in FIG. 1, a further alarm unit 44 is attached to the medical device 2 and provided to give an alarm. With respect thereto, in the fifth data base 37 from a plurality of different alarms a particular alarm is assigned to a specific location 4 where the medical device 2 is to be operated. In case of an alarm, the control unit 30 causes the alarm unit 44 to give an alarm corresponding to the particular alarm as assigned to the actual location 4a in the fifth data base 37. For doing so, the control unit 30 generates a specific alarm signal which is transferred from the interface 22 of the server 20 via the data link 24 and the interface 12 at the medical device 2 to the further alarm unit 44. So, the kind of alarm depends upon the actual position or location 4a where the medical device 2 is actually located so as in particular to facilitate a retrieval of the medical device 2.

In the embodiment as schematically shown in FIG. 1, the further alarm unit 44 also cooperates with a remote control 46 which is taken by a patient, a medical and/or nursing staff or any other person 48. At least one of the alarm unit 44 and the remote control 46 measures the distance therebetween and the alarm unit 44 changes the alarm in case of a change of said distance. For doing so, the alarm unit 44 and the remote control 46 are connected with each other by means of a wireless data link 50. Due to the change of the alarm in case of a change of said distance the patient or the medical and/or nursing staff or any other person 48 is guided to the medical device 2. When the remote control 46 and the medical device 2 with the alarm unit 44 are closer to each other than a predetermined minimum distance (e.g. 15 meters), both the alarm unit 44 and the remote control 46 give an alarm to ease the finding process.

Alternatively or additionally, the alarm unit 44 at the medical device 2 gives an alarm in case the positioning unit 6 determines a change of the actual geographical position of the medical device. For doing so, the alarm unit 44 is connected to the positioning unit 6. Due to this kind of alarm scenario attention is drawn to the medical device 2 if it is taken away e.g. by somebody who is not responsible. The same alarm function can be realized by additionally or alternatively using the alarm unit 32 of the server 20 in case the positioning unit 28 determines a change of the actual geographical position of the medical device 2.

Since the actual location 4*a* of the medical device 2 is known to the server 20, on a screen (not shown) of the alarm unit 32 indications can be given on a list including serial number, type, operating status and actual location 4*a* of the medical device 2 as well as medical devices which have not operated for several days so that the medical or nursing staff becomes able to search for them.

In the following the functioning of the above described system in accordance with an embodiment is explained in greater detail, in particular as to some further aspects.

As already mentioned above, used are devices incorporating a telemedicine service with the network server 20 and at least one portable medical device 2, in particular a drug infusion pump, either with integrated GSM/GPRS receiver, Wi-Fi and, optionally, RFID/NFC as Micrel Medical Devices Rythmic Cloud ambulatory infusion pump, or connected to a mobile phone or tablet which, by means of an application which provides the communication for triangulation either autonomously with individual AP location assignment and measurements (access point/position and strength) of as many access points as can be reached from a device, or through the provision of a service of a third party such as Google Maps Geolocation API or Skyhook. From Google Maps for a set of AP MAC/signal strength parameters and GSM/WMA mobile network parameters, a geolocation is received as a cross latitude, longitude line point and location on a map, so as to determine care areas such as Operating Room X, or Neonatal Y, Ward Z, etc. so that it is extremely easy and straightforward for a first time operation as it does not need any AP location finding.

Example of questions and answer of Google Maps API:

```
WiFi AP geolocation
{
  "macAddress": "01:23:45:67:89:AB",
  "signalStrength": -65,
  "age": 0,
  "channel": 11,
  "signalToNoiseRatio": 40
}
GSM geolocation
{
  "cellTowers": [
    {
      "cellId": 42,
      "locationAreaCode": 415,
      "mobileCountryCode": 310,
      "mobileNetworkCode": 410,
      "age": 0,
      "signalStrength": -60,
      "timingAdvance": 15
    }
  ]
}
WMA geolocation
{
  "cellTowers": [
    {
      "cellId": 21532831,
      "locationAreaCode": 2862,
      "mobileCountryCode": 214,
      "mobileNetworkCode": 7
    }
  ]
}
Response of Google Maps API
{
  "location": {
    "lat": 51.0,
    "lng": -0.1
```

-continued

```
  },
  "accuracy": 1200.4
}
```

Operation with individual three-dimensional triangulation measurements (optional) consists of measurements taken in areas of the hospital corresponding to the locations 4 as schematically shown in FIG. 1 (access point sniffing strength of signal) by means of Wi-Fi, which are recorded in the fourth database 36 at the server 20. In use, for each set of access points/signals measured by the device, the most likely Care Area of the hospital which maps with the actual location 4*a* is extracted from the server 20 by means of three-dimensional triangulation of sniffed (i.e. not necessarily connected) WiFi signals. Therefore, distance and access point location from the (optional) original recording of each exact AP location and the position/time and identity of the medical device 2 are recorded e.g. by referring to a serial number. Whereas a three-dimensional triangulation results in the determination of not only a geolocation, but also an altitude so as to even identify a specific floor, WiFi signals are received from all nearby WiFi access points in the same or nearby floors.

In addition, at the position where the medical devices 2 are stored in the hospital or at the homecare provider, the RFID/NFC or bar code scanner 42, or a bar code loading device with communication capabilities can take a measurement and send information to the server 20 or to a local computer about when the medical device 2 returned to or left the store or RFID tags on hospital locations 4 if contacted confirm the actual location 4*a* to the medical device 2, or the device itself asks for location confirmation. After all that, a knowledge is building in the system, where a specific pattern of strength of signals from respective access points is associated to a specific hospital care area, neonatal, operating room X, ICU Y, ward Z etc, so that by means of artificial intelligence using neural networks and trained by this feedback the location errors are reduced more and more with a continuation of use of the system so that a prediction of location needs no correction from the user anymore.

Operation with a third-party service is described by the provider of the service, in which case the medical device 2 or the sensing unit 38 connected thereto with appropriate communication capabilities (mobile phone or tablet), measures the strength of the signals at each mobile telephony or Wi-Fi access point and sends them to the server 20 which again sends them to the server of the third-party geolocation service together with the country of origin, mobile network, etc. as required by the specifications, and receives a geographical longitude and latitude and the measurement error expected (circle around the position). Once it receives them, they are stored in a database with the identification, which may be the serial number of the medical device 2. The server 20 can then display the pumps, position and/or time on a map of the third-party service, e.g. Google Maps, and recover from there the position, translated into an address, i.e. prefecture/town or city/street/number. In this way, with continuous latitude/longitude points, the movement of the portable medical device 2 can be displayed until the moment at which it is required, i.e. the present moment or another moment in the past. A device status can also be displayed like battery charge level, alarm status, last day in operation etc. So, the personnel can choose the most convenient medical device 2 to use in an emergency near-by.

Reproduced is the translation of the geographical position, longitude and latitude, at the position of use, i.e. position in a hospital, such as operating theatre, intensive care unit, recovery room, analgesia unit, etc. house living room, house bedroom, street, etc.

The medical device 2 can also have the capability for wireless communication (Bluetooth, Bluetooth LE, Wi-Fi, ANT protocol, NFC etc.) or wired communication with other devices such as mobile telephones and tablets that have GPS and to obtain its exact position from there and send it to the server 20 (mobile application).

The medical device 2 can also have or communicate equally with devices that have an altimeter, which identifies a floor in a multi-store building such as a hospital, which is also sent to the server 20. A specific floor can also be found by summing a signal strength from APs on each floor as known in US2005/0207381, or by means of a three-dimensional triangulation using access point location and altitude as described above or by processing signal strengths associated to confirmed positions (e.g. floor, room, bed) by barcode and/or RFID scanning or patient's confirmation as also described above.

A mobile application can obtain from the server 20 the positions of medical devices of a particular category or group of users situated close by (correlation of positions) and provide a service, using a compass (integrated in the mobile phone), similar to that of Nokia City Lens, in Windows Phone Lumia, which shows the position of restaurants and shops in the field of vision and displays an image taken by the camera of the room in the hospital and, depending on the direction the camera is facing, the camera shows the position of the devices and, as the case may be, basic information about the treatment, or alarms, or the imminent need for help, e.g. to change the bag in a drug infusion pump. Its use becomes even better with spectacles that project images, like Google glasses. The application can work at the simplest level by showing on a map the position of the observer (his mobile) with the devices around him on the same map.

Stationery medical devices such as large volumetric infusion pumps which are also called bedside pumps use complex patient data management systems which need a lot of configuration per therapy and location before an infusion can be done. This is convenient for stationery equipment, as configuration is done once and the medical device is rarely moved, but it is not convenient for ambulatory equipment to be used in several parts of the hospital. The telemedicine services provided by the server 20 are described in U.S. Pat. No. 8,551,038 B1 for facilitating the mobility of the medical device. Additional services relating to the use of a position are broken down into device geolocation and tracking services (sequential positions) over time, i.e. services to care providers, and the usability of a treatment/safety provided by the telemedical service by means of positioning so as to further ease the mobility of the medical device, such as a matchbox size full bedside pump described in US20140081202 and intended to be used wherever needed from the pocket of a medical or nursing staff.

In a first category, the aforementioned technology is used to record the movement of the medical device 2 each day. In this way, the medical device 2 is not lost. This makes it easier for medical devices not to be forgotten or stolen, which is currently a fear in hospitals as regards microscopic devices. For this to happen, the medical device 2 can (for periods of communication that are determined by means of configuration) appear switched off (OFF) externally, i.e. only the medical device's operational uses together with the screen and keypad switch off (e.g. if the medical device is an infusion pump, the infusion capabilities do not work) but internally the micro-processor wakes up in order to communicate with the points of access and the server 20 to record the position. This is called a 'state of sleep'. Sporadic, discontinuous communication does not consume enough energy for the battery to run low, while geolocation has certain advantages as already mentioned above. While the medical device 2 is 'sleeping', by tapping a key it is possible for the screen to display information such as the position (street/number, or area of a hospital), the patient who was last connected, the use that has been assigned, treatment, duration of sleep, and battery status. The server 20 finds out when the use of the medical device 2 has stopped from the events (ON-OFF, operation, and operating parameters, end of use) which it sent to it, and if after a reasonable period of time the medical device 2 has not returned to where it is stored, it notifies the persons responsible, so that a search for the medical device 2 can be initiated. If the medical device 2 returns to a store house, with or without exact RFID/NFC positioning confirmation, if there is no danger of it being removed (secure storage), then it can be securely switched off automatically (end of the state of sleep).

If the medical device 2 is very small, it may have a charger which communicates via Wi-Fi and/or GSM/GPRS and records its position at the same time as the basic telemedicine service, when it is connected to the charger.

Tracking is recorded in the log of the telemedicine service, i.e. when the medical device 2 went to the patient's house, in conjunction with when the treatment started, and what route the homecare nurse took. This information is useful for the insurance funds that ultimately pay for the services and for the homecare providers, which are sometimes the hospital itself. For companies providing homecare, the telemedicine service (server 20) displays a map with all the medical devices 2 that are in use and in storage and where they are located and, in a window, when you approach a dot, the type of medical device (model), the serial number, the hospital it is monitoring, the name of the doctor in attendance, the name of the patient, the name of the insurance company, address, telephone numbers, etc., even if a medical device has an alarm, changes colour or dot, and displays the name of the alarm for immediate intervention. A similar map can also be displayed for the hospital, where the medical devices appear in different operating areas of a hospital which are also called care areas and define the locations 4 as schematically shown in FIG. 1, e.g. intensive care unit, recovery room, theatre, etc., with similar scheduling and monitoring of actions. The colours and configurations of the dots can categorize the products by model, treatment or urgency of intervention, e.g. change of bag in a drug infusion pump in x minutes. It can call up a specific requested serial number, with a zoom which shows the area in magnification. Also, the route taken by every nurse who visits a number of patients can be proposed so that the best route can be programmed and then displayed in practice so that the company knows how the work is progressing at any particular time.

To find a medical device when it is 'sleeping', it can, receive a signal to sound the "detection" alarm so that it can be located easily in the area when searching people carrying the remote control 46 are approaching having a similar detection system locating them to the server 20.

The telemedicine server 20 can combine a position from the individual measurement and recording in the databases with the third-party positioning service for more accurate (lower error rate) positioning in large areas such as a hospital.

A second category defines patient location services. Awareness of the position of a patient who is in need of urgent medical care (device alarm) offers an automatic calling service or a service provided by the health workers of the nearest hospital or nursing service (first aid).

When medical devices consume consumables such as an infusion set of drug infusion pumps, when they are geolocated, i.e. the server 20 knows their geographical location, it gives information to the supplier about the place of consumption and, combining it with the quantity it takes from the device's log (e.g. a set was finished and replaced on such and such a date and at such and such a time), gives information on consumption geographically, i.e. facilitates the distribution and renewal of the stock without the need for the customer to place an order. This can take place using the final position of the distributing storage facility instead of the place of consumption, combining them with the commercial customer of the user of the information, e.g. the representative of a town, city or country, homecare company, etc.

The certification of the patient and his connection through the portable medical device 2 to the server 20 for treatment has certain advantages. Geolocation is used to further facilitate the process and to reduce the risk of medical error. When the medical device 2 arrives with the nurse at the house or in the vicinity of the hospital where the patient is located (position notified to the telemedicine support service) it receives a patient identification signal from the server 20, which compares the notified address and the geographical position of the device. The medical device 2 can display <<are you patient x?>> for confirmation and displays only the correct treatment protocol from the complete list of protocols that was programmed into it when it was in its base for ease of programming the day (all the medical devices obtain a complete list of protocols, i.e. programming just once instead of separately for each medical device) or, alternatively, it downloads the correct protocol from the internet in situ. The nurse can check and certify the patient and the protocol and other points of safety, such as the administration route of drugs in infusion pumps.

When the medical device 2 returns to its base it is disconnected from the patient in its schedule before it switches off, and so it is ready for another patient both as the same device of the reset log and at the server, where the medical device is now on the list of devices that are available for use. And a medical error is prevented because its certified geographical and physical position in the base also allows the patient to be changed both in the pump and at the server. The geographical location of a medical device 2 that is connected to a specific patient gives the location of the patient herself/himself if the patient needs to be transported as a matter of urgency (ambulance).

The location of a the medical device automatically recorded on a map by the system facilitates the journey of a new nurse to a house she does not know, the planning of the routes taken by nurses (planning), or, at a glance, a hospital nurse knows where to go to assist a patient.

Recording the location of a medical device and a patient in cases where the patient is mobile and has a portable medical device helps the doctor, by means of the telemedicine service, to find the patient, even for a reason other than monitoring the specific device or treatment.

The identification of a patient at the patient's home is easy because the portable medical device 2 knows the patient's address and also when he or she arrived at this address, in which case the identification and the choice of the correct treatment protocol (patient-centric programming) takes place automatically without error, especially when the medical device is small and the screen is not large enough for writing or for choosing a protocol.

In a third category there is an automatic device configuration per location.

Alarms: The automatic recognition of a location inside a hospital or outside, such as a house, facilitates use by automatically separating operations of the medical device for a hospital, where the nurses are present everywhere and aware of the problems of operation, from operations in the home, where the users generally want a simpler use both in terms of the medical device and the telemedicine support on the internet. For example, for alarms that cannot be used by the patient or relatives at home, they can be configured from a home care provider in accordance with the actual location 4a so that they do not sound at the patient's home but are sent to the server 20 and, by means of telemetry, e.g. by SMS or email, to an appropriate medical attendant, nurse or other medical personnel so that the specifications for specific alarms (such as e.g. EN6060102024) that must be in place are in compliance, and the persons without responsibility do not worry, while the alarms automatically return to normal operation if the medical device 2 arrives at a specific location 4 like a hospital (recognition of location). At some care areas in a hospital an attendant nurse may want the alarms to be sent to her computer or monitor, and not to sound at the patient. This can be configured in the fifth database 37 in the server 20 so that an automatic configuration per location takes place for medical devices in ambulatory use resulting in that the setup is greatly eased. This applies to all the following configuration types: libraries in use per department, access codes, lighting conditions and transportation.

Libraries in use per department: In addition, in the hospital, depending on the location or care area, e.g. postoperative, neonatal, oncology, the device downloads and automatically makes available the correct library of protocols and drug library for treatment ready for use without medication errors, that may result from a wrong protocol if the medical device 2 goes from one location 4 (FIG. 1) in the hospital to another location 4 (FIG. 1) where different treatments are carried out. In protocols included may infusion pump occlusion pressure levels which for intravenous or subcutaneous applications are different for adult patients or neonatal.

Access Codes: Safety access codes are used in pain control infusion pumps but not needed in a general ward where dextrose and/or electrolytes are used so as to keep veins open which is mainly the case, or in operating room when speed of operation is assured by well trained nurses.

Lighting conditions: In intensive care units (ICU and wards different lighting (display backlight) conditions are needed as in wards backlight may be turned off at night for the patient to sleep, but not in intensive care units where nurses need to take care of emergencies what is going wrong. So, lighting preferences can be automatically adjusted per location 4 or care area.

Transportation: In case a patient is transported from ICU or OR to wards, it continues with same configuration for the infusion but not for lighting or access parameters or alarm conditions that are changed to the new department preferences once the medical device 2 changes the location 4 and, hence, the care area.

In summary, in particular, if the medical device 2 is an infusion pump it may have the following behavior depending on its state:

1. OFF State:
   Geolocate the pump so that the server 20 can find the pump on a map.
   Communicate constitutive locations per determined time interval so that the server can trace mobility path.
   Activate an alarm on the pump to find it when searching people are approaching.
   By touching a screen or pressing a button giving battery status, name of the last patient, last date of use, department which the medical device belongs to, etc. on a screen so as to facilitate a new patient assignment procedure.

2. ON State:
   Validate location found, increase the system location precision (learning) progressively, associate a Care Area to a location data bundle (signal strength, access point).
   Configure according to location Care Area.
   Program according to configuration and department preferences, reduce medication errors and use patientcentric and locationcentric programming.

3. RUN State.
   Locate patient.
   Rescue patient.
   behave as per location Care Area configuration and preferences (lighting, alarms etc.).

The invention claimed is:

1. A system for locating and automatically setting a medical device to different operational modes, comprising:
   a medical device comprising (i) an interface configured to receive data and transmit position data at a signal strength to a computer system, wherein the signal strength is indicative of a strength of transmission of the position data from the medical device to the computer system, and (ii) positioning unit configured to determine a geographical position of the medical device, wherein the transmitted position data is data indicative of the determined geographical position; and
   the computer system comprising:
       a first database that correlates different operational modes of the medical device with, wherein the different locations are different spaces in an area where the medical device may be located;
       a second database that correlates the different locations with different geographical positions determined by the positioning unit;
       a third database that correlates the signal strength with sub-locations within the different locations, wherein each location of the different locations is subdivided into multiple sub-locations; and
       wherein, upon receipt of the position data from the medical device, the computer system, is configured to,
           (a) use the second database to assign a current location to the medical device based on the received position data,
           (b) use the first database to assign an operational mode to the medical device based on the current location assigned in step (a),
           (c) use the third database to assign a sub-location to the medical device based on the signal strength of the received position data, wherein the assigned sub-location is one of multiple regions within the current location assigned in step (a),
           (d) identify to a user, the current location assigned in step (a) and the sub-location assigned in step (c), and
           (e) set the medical device to the operational mode assigned in step (b).

2. The system according to claim 1, wherein the plurality different locations comprise operation theatres, intensive care units, wards in a hospital, rooms in a patient's home, and stores.

3. The system according to claim 1, further comprising: a sensing unit adapted to measure the signal strength.

4. The system according to claim 1, wherein the positioning unit is adapted to determine the geographical position of the medical device by triangulation of at least one of WiFi signals, WLAN signals, or cellular network signals.

5. The system according to claim 1, wherein the computer system is adapted to mark the geographical position of the medical device on a map.

6. The system according to claim 1, wherein the processing computer system is further adapted to determine a route taken by the medical device by recording a plurality of geographical positions of the medical device over a time interval.

7. The system according to claim 6, wherein the computer system is adapted to record the route on a map.

8. The system according to claim 1, wherein the medical device further comprises an altimeter and the computer system is further adapted to receive signals from the altimeter and identify a floor in a multi-story building where the medical device is located.

9. The system according to claim 1, further comprising: a scanner adapted to scan the medical device in a current location of the medical device.

10. The system according to claim 1, wherein the positioning unit is adapted to be in an activated state when the medical device is in a de-activated state.

11. The system according to claim 1, wherein the medical device further comprises an alarm unit configured to issue an alarm; and
   the computer system comprises a fifth database that correlates the different locations to different alarms, and the computer system is further configured to direct the alarm unit to issue an alarm corresponding to the alarm assigned in the fifth database to the single location assigned to the medical device in step (a).

12. The system according to claim 1, wherein the system further comprises a remote control adapted to activate the alarm unit, wherein the alarm unit is configured to change a characteristic of the issued alarm in response to a change of distance between the alarm unit and the remote control.

13. The system according to claim 1, wherein the medical device further comprises an alarm unit connected to the positioning unit and adapted to issue an alarm in response to the positioning unit determining a change of the determined geographical position of the medical device.

14. The system of claim 1, wherein the computer system further includes a fourth database that correlates operating data, including at least one of operating protocols and drug libraries, with the different locations, and the computer server is further configured to (f) use the fourth database to assign at least one operating data to the medical device based on the current location assigned in step (a).

15. A system for locating one or more medical devices in a building, comprising:
   a medical device, wherein the medical device includes:

(i) a positioning unit configured to determine a geographical position of the medical device in the building;

(ii) an interface unit configured to transmit position data to a computer system, the position data being data indicative of the determined geographical position; and the computer system configured to:
(a) receive the position data at a signal strength from the medical device;
(b) determine a device-location by correlating the received position data in step (a) with data representative of different physical locations in the building, the determined device-location being one of multiple locations in the building that the medical device may be currently positioned in;
(c) determine a device sub-location by correlating the signal strength of the position data received in step (a) with data representative of signal strengths of transmissions by the medical device from different sub-locations within the device-location determined in step (b), wherein the determined device sub-location is one sub-location of multiple sub-locations, within the determined device-location, that the medical device may be currently positioned in; and
(d) identify, to a user, the determined device-location and device sub-location of the medical device.

16. The system of claim 15, wherein the computer system is further configured to assign an operating mode to the medical device based on the device-location determined in step (b), the assigned operating mode being one operating mode of multiple operating modes that the medical device can operate in.

17. The system of claim 15, wherein the medical device is a first medical device, the system further including a second medical device, and the computer system is further configured to:
determine a device-location and a device sub-location of the second medical device; and
identify, to the user, the determined device-location and device sub-location of the second medical device.

18. A method of locating one or more medical devices in a building, comprising:
(a) receiving, at a computer system, position data at a signal strength from a medical device, the position data being data indicative of a geographical position of the medical device in the building;
(b) determining a device-location by correlating the received position data in step (a) with data representative of different physical locations in the building, the determined device-location being one location of multiple locations in the building that the medical device may be currently positioned in;
(c) determining a device sub-location by correlating the signal strength of the position data received in step (a) with data representative of signal strengths of transmissions by the medical device from different sub-locations within the device-location determined in step (b), wherein the determined device sub-location is one sub-location of multiple sub-locations, within the determined device-location, that the medical device may be currently positioned in; and
(d) identifying, to a user, the determined device-location and device sub-location of the medical device.

19. The method of claim 18, further including (e) assigning an operating mode to the medical device based on the device-location determined in step (b), the assigned operating mode being one operating mode of multiple operating modes that the medical device can operate in.

20. The method of claim 18, wherein the medical device is a first medical device, and the method further includes:
receiving, at the computer system, position data at a signal strength from the second medical device;
determining a device-location and a device sub-location of the second medical device; and
identifying, to the user, the determined device-location and device sub-location of the second medical device.

* * * * *

UNITED STATES PATENT AND TRADEMARK OFFICE
CERTIFICATE OF CORRECTION

PATENT NO. : 10,874,796 B2
APPLICATION NO. : 14/559304
DATED : December 29, 2020
INVENTOR(S) : Achilleas Tsoukalis It is certified that error appears in the above-identified patent and that said Letters Patent is hereby corrected as shown below:

In the Claims

Column 17, Line 38, in Claim 1, delete "positioning" and insert --a positioning--.
Column 17, Line 44, in Claim 1, delete "with" and insert --with different locations--.
Column 18, Line 6, in Claim 2, delete "plurality.".
Column 18, Lines 20-21, in Claim 6, delete "processing.".

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*